United States Patent
Kuroda et al.

(10) Patent No.: US 7,056,526 B2
(45) Date of Patent: Jun. 6, 2006

(54) MEDICAL ADHESIVE COMPOSITION, MEDICAL ADHESIVE TAPE USING THE SAME AND TAPE PREPARATION FOR PERCUTANEOUS ABSORPTION

(75) Inventors: Hidetoshi Kuroda, Ibaraki (JP); Takateru Muraoka, Ibaraki (JP); Keigo Inosaka, Ibaraki (JP); Hitoshi Akemi, Ibaraki (JP)

(73) Assignee: Nitto Denko Corporation, Ibaraki (JP)

( * ) Notice: Subject to any disclaimer, the term of this patent is extended or adjusted under 35 U.S.C. 154(b) by 490 days.

(21) Appl. No.: 10/230,495

(22) Filed: Aug. 29, 2002

(65) Prior Publication Data

US 2003/0049440 A1    Mar. 13, 2003

(30) Foreign Application Priority Data

Aug. 29, 2001  (JP)  ............................. 2001-259970

(51) Int. Cl.
*A61K 9/70*    (2006.01)
(52) U.S. Cl. .................. 424/443; 424/445; 424/447; 424/448; 424/449; 428/343; 524/386; 524/388
(58) Field of Classification Search ................ 424/443, 424/445, 447, 448, 449; 428/343; 524/386, 524/388
See application file for complete search history.

(56) References Cited

U.S. PATENT DOCUMENTS

| 3,532,708 | A | * | 10/1970 | Blance ........................ 524/300 |
| 3,740,366 | A | * | 6/1973 | Sanderson et al ........... 524/398 |
| 3,886,126 | A | * | 5/1975 | McKenna, Jr. .............. 524/357 |
| 4,185,051 | A | * | 1/1980 | McKenna et al. ........... 525/370 |
| 4,234,660 | A | * | 11/1980 | McKenna et al. ........... 428/356 |
| 4,442,258 | A | * | 4/1984 | Sunakawa et al. ........... 524/767 |
| 4,987,186 | A | * | 1/1991 | Akiyama et al. ............ 525/107 |
| 5,298,258 | A | | 3/1994 | Akemi et al. |
| 5,648,166 | A | | 7/1997 | Dunshee |
| 5,876,745 | A | * | 3/1999 | Muraoka et al. ............. 424/448 |
| 6,077,528 | A | | 6/2000 | Muraoka et al. |
| 6,139,867 | A | * | 10/2000 | Muraoka et al. ............. 424/448 |

FOREIGN PATENT DOCUMENTS

| CN | 1219874 A | 6/1999 |
| DE | 43 03 616 C1 | 8/1994 |

\* cited by examiner

Primary Examiner—Bernard Lipman
(74) Attorney, Agent, or Firm—Leydig, Voit & Mayer, Ltd.

(57) ABSTRACT

The present invention provides a medical adhesive tape and a tape preparation for percutaneous absorption, both having an adhesive layer that resists glue remainder and stickiness upon peeling off of the tape even after adhesion to the human skin for a long time, and a medical adhesive composition to be used for such tapes. The medical adhesive composition of the present invention includes, as essential elements, (A) a copolymer containing (a) alkyl (meth)acrylate, wherein the alkyl moiety has 4 to 18 carbon atoms, in a proportion of not less than 50 wt % of the copolymer and (b) a carboxyl group-containing vinyl compound in a proportion of 0.1 wt %–10 wt % of the copolymer, (B) an alkoxide or a chelate compound of at least a metal selected from titanium, zirconium, zinc and aluminum, and (C) a polyol compound in a proportion of 0.2 wt %–5 wt % of the aforementioned medical adhesive composition. The medical adhesive tape of the present invention and tape preparation for percutaneous absorption are characterized in that the adhesive layer contains the above-mentioned medical adhesive composition of the present invention.

8 Claims, No Drawings

MEDICAL ADHESIVE COMPOSITION, MEDICAL ADHESIVE TAPE USING THE SAME AND TAPE PREPARATION FOR PERCUTANEOUS ABSORPTION

FIELD OF THE INVENTION

The present invention relates to a medical adhesive tape to be adhered to the skin for the protection of or fixing an object to the skin, a tape preparation for percutaneous absorption to administer a drug to the body through the skin, and a medical adhesive composition therefor.

BACKGROUND OF THE INVENTION

The adhesive layer of a medical adhesive tape to be adhered to the human skin for the protection of the skin, fixing something to the skin and the like, and a tape preparation for percutaneous absorption to administer a drug to the body through the human skin (preparation for percutaneous absorption) is required to have a sufficient adhesive force for adhesion to the skin, as well as the property to allow release or removal from the skin surface (cohesive force) after use, without staining (glue remainder and stickiness). The balance between the adhesive force and the cohesive force of such adhesive layer can be controlled by a suitable crosslinking treatment of an adhesive to be used, and various crosslinking treatments have been conventional by tried. As a crosslinking treatment of an adhesive, there are mentioned physical crosslinking by irradiation such as UV irradiation, electron beam irradiation and-the like, chemical crosslinking using a crosslinking agent such as polyfunctional isocyanate, organic peroxides, organometal compound, metal alkoxide, metal chelate compound, polyfunctional compound and the like, and the like.

Of the above-mentioned crosslinking treatments of the adhesive, however, the use of irradiation, organic peroxide or polyfunctional isocyanate sometimes results in a failure to cause-a crosslinking reaction or markedly low crosslinking efficiency, depending on the properties of the adhesive and the kind of additive. By these crosslinking treatments, moreover, a tape preparation for percutaneous absorption wherein an adhesive layer contains a drug may show decomposition of the drug to decrease the drug content.

It is known that, when a crosslinking agent, such as the aforementioned metal alkoxide and metal chelate compound, is used, such problems are not caused and a crosslinking treatment is affordable. However, the investigations by the present inventors have confirmed that an adhesive tape that has been crosslinked by the use of metal alkoxide or a metal chelate compound, particularly an adhesive tape containing a large amount of a plasticizer component, shows, after adhesion to the human skin surface for a long time, a cohesive force that was decreased with the lapse of time, which in turn results in a dramatic increase in the adhesive force during peeling off and staining of the skin surface (glue remainder, stickiness) due to the disintegration of the adhesive layer. While the occurrence of this phenomenon varies depending on the interindividual difference in the case of a relatively short period of application of within 24 hours, but observed at an extremely high frequency in the case of a long-term application of 48 hours or longer, irrespective of the interindividual difference.

The above-mentioned glue remainder and stickiness on the skin can be removed by wiping the skin with an alcohol solvent and the like. However, this wiping treatment is troublesome and some adhesive layers resist complete removal. Particularly in the case of a tape preparation for percutaneous absorption, an adhesive remainder on the skin may permit the drug in the residue to unexpectedly show efficacy even after removal of the preparation, which is potentially dangerous.

To deal with a cohesive failure during a long-term application to the human skin, it may be possible to increase the concentration of a crosslinking agent in the adhesive composition to increase crosslinking density, thus enhancing the initial cohesive force, and maintain a practical cohesive force even after a long-term application. However, an increased crosslinking density may cause a lower initial adhesive force (tackiness) to the skin, an increased amount of a crosslinking agent may shorten a pot life or produce a drug decomposition product and other problems.

As mentioned earlier, application for 24 hours or shorter does not generally cause a particularly serious problem, because the occurrence of glue remainder or stickiness varies depending on the interindividual difference. However, a function to stand a continuous application for a comparatively long period (not shorter than 2 days, sometimes about a week) has been increasingly requested in recent years for a medical adhesive tape or a tape preparation for percutaneous absorption to have. Thus, there is a demand for a medical adhesive tape or a tape preparation for percutaneous absorption having an adhesive layer that resists glue remainder and stickiness upon peeling off of the tape even after adhesion to the human skin for a long time of 48 hours or longer.

SUMMARY OF THE INVENTION

It is therefore an object of the present invention to provide a medical adhesive tape or a tape preparation for percutaneous absorption, which has an adhesive layer that resists glue remainder and stickiness upon peeling off of the tape even after adhesion to the human skin for a long time, and a medical adhesive composition to be used for such tapes.

The present inventors have considered that a number of sebaceous matters and secretions present on the skin surface of a healthy individual (Dermatology, $6^{th}$ ed.: Kenichi Ueno, Kinpoudou (1996), p 15–16, p18) include a substance that causes glue remainder (cohesive failure) and investigated to find that lactic acid, which is among the secretions in human perspiration, is most influential. That is, when lactic acid is brought into contact with an adhesive composition crosslinked by a metal alkoxide or a metal chelate compound, a time-course increase in the adhesive force and a cohesive failure occur. It has been further found that this phenomenon also occurs in α-hydroxy acid (glycolic acid and the like) having a hydroxyl group at the α-position, besides lactic acid. This suggests that in an adhesive containing a metal alkoxide or a metal chelate compound, the metal is bonded to a carboxyl group in the adhesive to form crosslinking, and once a compound that is easily chelated with a metal, such as α-hydroxy acid, enters from the outside, the metal bonded to the carboxyl group of the adhesive is chelated by the aforementioned compound that entered from the outside, thus causing the decrease in the above-mentioned cohesive force (cohesive failure).

Based on the these findings, the present inventors have further found that a decrease in the cohesive force due to the contact with lactic acid present on the human skin and a decrease in the cohesive force during a long time application to the human skin can be remarkably inhibited by the addition of a small amount of a polyol compound as a crosslinking stabilizer to the adhesive tape.

Accordingly, the present invention relates to the following.

(1) A medical adhesive composition comprising the following (A) to (C) as essential components:
(A) a copolymer comprising the following (a) and (b) as copolymerized monomers,
(a) alkyl (meth)acrylate, wherein the alkyl moiety has 4 to 18 carbon atoms, in a proportion of not less than 50 wt % of the copolymer,
(b) a carboxyl group-containing vinyl compound in a proportion of 0.1 wt %–10 wt % of the copolymer,
(B) an alkoxide or a chelate compound of at least a metal selected from titanium, zirconium, zinc and aluminum, and
(C) a polyol compound in a proportion of 0.2 wt %–5 wt % of the aforementioned medical adhesive composition.
(2) The medical adhesive composition of the above-mentioned (1), wherein the copolymer (A) further comprises
(c) a vinyl compound free of carboxyl group, which is copolymerizable with the above-mentioned alkyl (meth)acrylate (a) and the above-mentioned carboxyl group-containing vinyl compound (b),
in a proportion of not more than 49.9 wt % of the copolymer as a copolymerized monomer.
(3) The medical adhesive composition of the above-mentioned (1) or (2), further comprising a plasticizer (D) compatible with the copolymer (A), wherein a content weight ratio of the plasticizer (D) to the copolymer (A) ((D)/(A)) is 0.25–2.0.
(4) The medical adhesive composition of any of the above-mentioned (1) to (3), wherein the polyol compound (C) is at least one kind selected from glycerol and propylene glycol.
(5) A medical adhesive tape to be applied to a human skin, which comprises an adhesive layer made from the medical adhesive composition of any of the above-mentioned (1) to (4).
(6) A tape preparation for percutaneous absorption, comprising a medical adhesive tape of the above-mentioned (5), wherein said adhesive layer further comprises a drug to be administered by percutaneous absorption.

DETAILED DESCRIPTION OF THE INVENTION

The present invention is explained in detail in the following.

In the present specification, the "medical adhesive tape" is a tape to be adhered to the human skin for a medical purpose, which embraces a "tape preparation for percutaneous absorption" further containing a drug to be administered by percutaneous absorption, and a tape free of a drug (e.g., a supporter to protect the skin, a tape to immobilize a catheter on the skin and the like. As used herein, the "medical purpose" means treatment or prophylaxis of diseases and injuries. The "medical adhesive tape" may contain a drug (e.g., antibacterial agent, antipruritic drug etc.) other than the drug to be administered by percutaneous absorption. In the present specification, the "medical adhesive composition" means a composition free of the drug to be administered by percutaneous absorption, which can adhere to the human skin and can be used for the above-mentioned "medical adhesive tape".

The medical adhesive composition of the present invention contains, as essential components, a copolymer (A) containing a particular alkyl (meth)acrylate (a) and a carboxyl group-containing vinyl compound (b) as copolymerized monomers, a metal alkoxide or chelate compound (B), and a polyol compound (C).

The alkyl (meth)acrylate (a), which is a copolymerized monomer of copolymer (A), contains an alkyl group having 4 to 18, preferably 4 to 12, carbon atoms. When the alkyl group of the alkyl (meth)acrylate has not more than 3 or not less than 19 carbon atoms, an adhesive having a sufficiently low glass transition temperature to afford fine tackiness as an adhesive tape cannot be obtained easily.

Examples of the alkyl (meth)acrylate (a) include those containing linear chain alkyl group, branched alkyl group and the like, such as butyl, pentyl, hexyl, heptyl, octyl, nonyl, decyl, undecyl, dodecyl, tridecyl and the like. The alkyl (meth)acrylate can be used alone or in combination of two or more.

The alkyl (meth)acrylate (a) to be used in the present invention is preferably alkyl (meth)acrylate wherein the alkyl moiety has 4 to 8 carbon atoms, because it lowers the glass transition temperature and imparts stickiness at ambient temperature. Examples of such alkyl (meth)acrylate include butyl acrylate, 2-ethylhexyl acrylate, 2-ethylhexyl methacrylate, cyclohexyl acrylate, cyclohexyl methacrylate and the like, with particular preference given to 2-ethylhexyl acrylate, because its homopolymer has a sufficiently low glass transition temperature (–70° C.) and it is commercially available. The aforementioned homopolymer preferably has a glass transition temperature of –80° C. to –40° C., more preferably –70° C. to –50° C.

The copolymer (A) contains the above-mentioned alkyl (meth)acrylate (a) in a proportion of not less than 50 wt % as a copolymerized monomer. When the content of alkyl (meth)acrylate (a) in the copolymer (A) is less than 50 wt %, the copolymer loses sufficient tackiness for use as an adhesive. In view of the better tackiness, the copolymer (A) preferably has an alkyl (meth)acrylate (a) content of not less than 70 wt %.

When the copolymer A has too great an alkyl (meth) acrylate (a) content, the copolymer (A) shows properties similar to those of alkyl (meth)acrylate (a) alone and cannot provide a useful adhesive, which necessitates modification by adding other monomers to be mentioned later. From this viewpoint, copolymer component (A) preferably has an alkyl (meth)acrylate (a) content of not more than 99 wt %, more preferably not more than 95 wt %.

In the present invention, a carboxyl group-containing vinyl compound (b), which is a monomer having a functional group capable of forming a crosslinking point when using the metal alkoxide or chelate compound to be mentioned later, is used as a second monomer to be copolymerized with the above-mentioned alkyl (meth) acrylate (a) in copolymer (A). Examples of such carboxyl group-containing vinyl compound (b) include (meth)acrylic acid, itaconic acid, maleic acid, mesaconic acid, citraconic acid, glutaconic acid and the like.

The copolymer (A) contains the above-mentioned carboxyl group-containing vinyl compound (b) in a proportion of 0.1 wt %–10 wt %, preferably 1 wt %–5 wt %, as a copolymerized monomer. When the content of the carboxyl group-containing vinyl compound (b) in copolymer (A) is less than 0.1 wt %, crosslinking points become less and an adhesive layer having a sufficient cohesive force cannot be obtained. When the content of the carboxyl group-containing vinyl compound (b) in copolymer (A) exceeds 10 wt %, skin irritation may be caused by the carboxyl group.

The metal alkoxide or metal chelate compound (B) is used in the medical adhesive composition of the present invention as a crosslinking agent for the crosslinking treatment of the above-mentioned copolymer (A). As the metal of the metal alkoxide or metal chelate compound (B), at least one of titanium, zirconium, zinc and aluminum is used in view of the fine reactivity and handling property, with preference given to a chelate compound such as aluminum and titanium. Since these crosslinking agents (B) do not increase viscosity of coating solution, the workability is extremely superior.

The metal alkoxide or metal chelate compound (B) of the medical adhesive composition of the present invention is preferably added in a proportion of 0.01 part by weight –2.0 parts by weight, more preferably 0.05 part by weight –0.5 part by weight, per 100 parts by weight of the copolymer (A). When the metal alkoxide or metal chelate compound (B) is less than 0.01 part by weight per 100 parts by weight of the copolymer (A), an adhesive layer having a sufficient cohesive force during use as a medical adhesive tape or a tape preparation for percutaneous absorption may not be obtained. When the metal alkoxide or metal chelate compound (B) exceeds 2.0 parts by weight per 100 parts by weight of the copolymer (A), the initial adhesive force (tackiness) to the skin may be unpreferably reduced, or skin irritation due to the residual unreacted crosslinking agent may be easily expressed or a drug decomposition product may be produced.

The adhesive layer gelled by the metal alkoxide or metal chelate compound (B) preferably has a gel fraction of 60 wt %–80 wt %, more preferably 65 wt %–78 wt %. When the gel fraction of the above-mentioned adhesive layer is less than 60 wt %, a cohesive force sufficient for an adhesive layer cannot be imparted, a glue remainder and strong skin irritation due to cohesive failure are tend to be expressed upon peeling. When the gel fraction of the above-mentioned adhesive layer exceeds 80 wt %, the cohesive force may become high but a sufficient skin adhesive force may not be obtained. The gel fraction of this adhesive layer can be adjusted by controlling the amount of the crosslinking agent, as generally employed in the pertinent field.

The polyol compound (C) in the medical adhesive composition of the present invention is a polyhydric alcohol compound having two or more, preferably 2 or 3 hydroxyl groups, in one molecule, and is used as a crosslinking stabilizer of the above-mentioned copolymer (A). Examples of the polyol compound (C) include glycols such as ethylene glycol, diethylene glycol, triethylene glycol and dipropylene glycol, diols such as 1,3-butanediol, 1,4-butanediol, 2-ethyl-1,3-hexanediol and propylene glycol, triols such as glycerol, 1,2,6-hexane triol and the like, amino alcohols such as diethanolamine, triethanolamine, diisopropanolamine and triisopropanolamine, polyol esters such as glycerol fatty acid monoester, sorbitan fatty acid monoester and sucrose fatty acid ester, and the like.

The polyol compound (C) is preferably compatible with the above-mentioned copolymer (A), but complete compatibility with copolymer (A) is not necessarily essential, as long as a significant influence is not found on the adhesive property. Conversely, the use of a polyol compound having a low boiling point results in a lower content due to volatilization during coating and drying for formulation of the preparation, which may prevent expression of a cohesive failure inhibitory effect. As the polyol compound (C), therefore, those having a boiling point at an atmospheric pressure (generally 1 atm) of not less than 150° C. are preferably used.

The content of polyol compound (C) in the medical adhesive composition of the present invention varies depending on the content of the carboxyl group of copolymer (A) and the concentration of a metal alkoxide or metal chelate compound (B) to be added. It is generally 0.2 wt %–5 wt %, preferably 0.3 wt %–1 wt %, more preferably 0.3 wt %–0.5 wt %, of the entire medical adhesive composition. When the content of the polyol compound (C) is less than 0.2 wt % of the entire medical adhesive composition, a crosslinking-stabilizing effect cannot be exerted sufficiently. When the content of the polyol compound (C) exceeds 5 wt % of the entire medical adhesive composition, the probability of reaction between a metal alkoxide or metal chelate compound (B) and the hydroxyl group of the polyol compound (C) becomes high, and the objective crosslinking reaction is not easily caused, thus failing to provide a sufficient cohesive force to the adhesive layer, or in the case of a tape preparation for percutaneous absorption, it gives an adverse influence on the releaseability and solubility of a drug.

When the amount of addition of the polyol compound (C) is within the above-mentioned range, an adverse influence on the adhesive property, releaseability and solubility of the drug can be almost ignored. To eliminate the above-mentioned adverse influence, the content of polyol compound (C) is preferably made as small as possible (particularly preferably about 0.3 wt %–0.5 wt % of the entire medical adhesive composition as mentioned above). Therefore, at least one kind of glycerol and propylene glycol is particularly preferably used as the polyol compound (C). This is because glycerol and propylene glycol have a high hydroxyl group content per unit weight and the addition of a trace amount as mentioned above can afford a superior effect as a crosslinking stabilizer.

The medical adhesive composition of the present invention basically has the aforementioned composition and can provide an adhesive that does not easily cause glue remainder or stickiness upon peeling thereof after adhesion to the human skin for a long time, such as about 48 hr–120 hr. This is considered to be attributable to the aforementioned composition, wherein an action as a medical adhesive composition is not inhibited due to the presence of polyol compound (C), and elimination of crosslinking due to the contact between a metal alkoxide or metal chelate compound (B) and α-hydroxy acid present on the human skin can be prevented. Therefore, lowering of the cohesive force of an adhesive can be remarkably inhibited even in the case of a long-term application to the human skin.

The medical adhesive composition of the present invention can be preferably used for an adhesive layer of, for example, a medical adhesive tape to be adhered to the human skin. The duration of application of the medical adhesive tape of the present invention to the human skin is not particularly limited. In view of the aforementioned problems in the conventional medical adhesive tapes, the present invention is particularly useful for adhesion for a long time. As used herein, adhesion for a long time means, adhesion for a period of not less than 24 hours, preferably 48 to 96 hours.

The adhesive layer of the medical adhesive tape can be formed by, for example, applying the above-mentioned medical adhesive composition onto a support by coating, drying in a dryer at, for example, 100° C. for 3 min and standing the resulting product in a thermostat incubator at, for example, 70° C. for 48 hours to allow progress of crosslinking reaction.

The support to be used for the medical adhesive tape of the present invention is not particularly limited and those formed from various materials conventionally used widely in this field can be used. A support free of a decrease in the contents of the components in the adhesive layer as a result of volatilization from the back of the support and the like, in other words, a support formed from a material that does not allow permeation of these components is preferable. Examples of the material used for forming such support include single films of polyester, nylon, saran, polyethylene, polypropylene, ethylene-polyvinyl acetate copolymer, polyvinyl chloride, ethylene-ethyl acrylate copolymer, polytetrafluoroethylene, Surlyn, metal foil and the like, and laminate films thereof and the like.

The medical adhesive tape of the present invention is preferably made by forming an adhesive layer on a porous sheet of a support obtained by laminating a nonporous sheet comprising the above-mentioned material on a porous sheet. When such support is used, adhesion between a support and an adhesive layer (anchor effect) can be enhanced, and a medical adhesive tape particularly superior in the effect of preventing the release of a support from an adhesive layer, as often found in the edge part (corner), can be afforded.

As the above-mentioned porous sheet, any can be used without any particular limitation as long as the anchor effect with the adhesive layer can be improved, and for example, paper, woven fabric, nonwoven fabric, mechanically perforated sheet and the like can be used, with particular preference given to paper, woven fabric and nonwoven fabric. The porous sheet generally has a thickness of 10 μm–500 μm, for the improvement of an anchor effect and flexibility of the adhesive layer. When woven fabric and nonwoven fabric are used as the above-mentioned porous sheet, the sheet preferably has a basic weight of 5 $g/m^2$–30 $g/m^2$, more preferably 8 $g/m^2$–20 $g/m^2$, for an improved anchor effect.

The medical adhesive tape of the present invention may further contain, in an adhesive layer thereof, a drug to be administered by percutaneous-absorption, and can be used as a tape preparation for percutaneous absorption. While the tape preparation for percutaneous absorption of the present invention poses no particularly limitation on the adhesion time, it is particularly useful for a long time adhesion.

The above-mentioned drug to be administered by percutaneous absorption in the tape preparation for percutaneous absorption of the present invention can be determined freely according to the object thereof. For example, a drug that can be administered by percutaneous absorption from among the drugs of the kinds of corticosteroides, analgesis antiphlogistic, somnifacient sedative agent, tranquilizer, antihypertensive, hypotensive diuretic, antibiotic, anesthetic, antimicrobial, antifungal agent, vitamin agent, coronary vasodilator, antihistamine, sex hormone agent, antiemetic, cough medicine and the like is selected. These drugs can be used in combination of two or more kinds as necessary.

The content of the above-mentioned drug in the tape preparation for percutaneous absorption of the present invention can be determined as appropriate according to the kind of drug and administration object. It is generally preferably about 1 wt %–40 wt %, more preferably about 3 wt %–30 wt % of the adhesive layer. When the content of the above-mentioned drug is less than 1 wt % in the adhesive layer, the release of an amount effective for the treatment may not be expected. The content of the drug in a proportion exceeding 40 wt %, of the adhesive layer does not show an improvement in the treatment effect due to the increased amount of the drug, and is economically meaningless.

As a support for forming an adhesive layer of the tape preparation for percutaneous absorption of the present invention, those used for the above-mentioned medical adhesive tape can be preferably used.

In the medical adhesive composition of the present invention, the above-mentioned copolymer (A) may contain, as an optional monomer in addition to the above-mentioned alkyl (meth)acrylate (a) and carboxyl group-containing vinyl compound (b), a vinyl compound (c) free of a carboxyl group and copolymerizable therewith. Such vinyl compound (c) free of carboxyl group can be used for controlling the cohesive force of an adhesive layer of the objective medical adhesive tape or tape preparation for percutaneous absorption, and for controlling solubility and releaseability of the drug and the like in the case of a tape preparation for percutaneous absorption.

Examples of such vinyl compound (c) include vinyl esters such as vinyl acetate and vinyl propionate, vinyl ethers such as methylvinyl ether and ethylvinyl ether, vinyl amides such as N-vinyl-2-pyrrolidone and N-vinyl caprolactam, hydroxy group-containing monomers such as hydroxyethyl (meth) acrylate, hydroxypropyl (meth)acrylate and α-hydroxymethyl acrylate, amide group-containing monomers such as (meth)acrylamide and dimethyl (meth)acrylamide, alkoxyl group-containing monomers such as methoxyethyl (meth) acrylate and ethoxyethyl (meth)acrylate, and vinyl monomers such as styrene, vinyl pyridine, vinyl imidazole, vinyl morpholine and the like.

When such vinyl compound free of carboxyl group (c) is contained in copolymer (A) as a copolymerized monomer, its content needs to be not more than 49.9 wt %, in view of the relationship between the essential components, the content of alkyl (meth)acrylate (a) and carboxyl group-containing vinyl compound (b). While the above-mentioned vinyl compound (c) can be contained in copolymer (A) in an optional proportion of not more than 49.9 wt %, it is contained in a proportion of not more than 30 wt % of copolymer (A), to inhibit an adverse influence on the adhesive property of copolymer (A). For full expression of the effect of modification of copolymer (A) by the addition of the above-mentioned vinyl compound (c), the above-mentioned vinyl compound (c) is preferably contained in a proportion exceeding 1 wt %, more preferably exceeding 5 wt %, of copolymer (A).

The medical adhesive composition of the present invention preferably further contain plasticizer (D) compatible with copolymer (A). The weight ratio for addition of the plasticizer (D) to the copolymer (A) (content ratio (D)/(A)) is preferably 0.25–2.0, more preferably 0.4–1.8, particularly preferably 0.6–1.8, for the reduction of skin irritation. That is, for reduction of skin irritation caused by the adhesive layer of the medical adhesive composition of the present invention, the plasticizer (D) is preferably contained in a large amount.

The addition of plasticizer (D) imparts softness by plasticizing an adhesive layer formed from the medical adhesive composition, and reduces pain and skin irritation caused by adhesion to the skin when peeling off the medical adhesive tape or tape preparation for percutaneous absorption comprising the composition from the skin. Thus, plasticizer (D) to be used in the present invention needs to show only a plasticizing action. When it is used as an adhesive layer of the tape preparation for percutaneous absorption, one having a percutaneous absorption promoting action is preferably used for improving the percutaneous absorption of the drug contained in the adhesive layer. When a polyol compound is used for the plasticizer (D), crosslinking due to a metal alkoxide or metal chelate compound does not occur at all, or the efficiency thereof is considered to be greatly decreased. In the present invention, addition of a polyol compound beyond the aforementioned content for achieving the plasticizing action is not preferable.

Accordingly, the compound preferably used as a plasticizer (D) in the present invention is exemplified by fats and oils such as olive oil, castor oil, squalene and lanolin, organic solvents such as dimethyldecyl sulfoxide, methyloctyl sulfoxide, dimethyl sulfoxide, dimethylformamide, dimethyl acetamide, dimethyl lauramide, N-methyl-2-pyrrolidone and dodecylpyrrolidone, liquid surfactants, plasticizers such as diisopropyl adipate, phthalic acid esters and diethyl sebacate, hydrocarbons such as liquid paraffin, fatty acid esters such as ethyl oleate, diisopropyl adipate, isopropyl palmitate, octyl palmitate, isopropyl myristate, isotridecyl myristate, ethyl laurate and the like, and glycerol fatty acid ester, propylene glycol fatty acid ester, ethoxy stearyl alcohol, pyrrolidonecarboxylic acid fatty acid ester and the like. One of these may be added for use.

EXAMPLES

The present invention is explained in detail by referring to Examples. These are mere examples and do not limit the present invention in any way.

[1] Example and Comparative Examples of Medical Adhesive Tapes

Example 1

2-Ethylhexyl acrylate (99.5 parts by weight, TOAGOSEI Co., Ltd.), acrylic acid (0.5 part by weight, TOAGOSEI Co., Ltd.), ethyl acetate (100 parts by weight, Wako Pure Chemical Industries, Ltd.) and benzoyl peroxide (0.2 part by weight, NYPER BW, NOF CORPORATION) were reacted in a separable flask equipped with a condenser, a stirrer, a thermometer, a dropping funnel and a nitrogen inlet tube at 60° C. for 15 hr under a nitrogen atmosphere to give a copolymer solution. To the copolymer solution (solid content 99.5 parts by weight) were added 0.5 part by weight of glycerol (Wako Pure Chemical Industries, Ltd.) and 20 parts by weight of isopropanol (Wako Pure Chemical Industries, Ltd.), which was followed by stirring.

To this solution was added 0.3 part by weight of ethyl acetoacetate aluminum diisopropylate (ALCH (Kawaken Co., Ltd.)) as a 5% isopropanol/ethyl acetoacetate (9/1(v/v)) solution.

The obtained solution was applied to a nonwoven fabric side of a support comprising a polyester nonwoven fabric (basic weight: 12 g/m$^2$) having a 2 μm thick polyethylene terephthalate film extrusion-formed thereon, to form an adhesive layer in the thickness of 80 μm and dried. For applying the adhesive, Baker applicator YBA-2 type (YOSHIMITSU SEIKI Co., Ltd.) was used. For drying the adhesive, Fine Oven DF-62 (YAMATO SCIENTIFIC CO., LTD.) was used at 100° C. for 3 min. The adhesive layer thus formed was adhered to a polyester film (75 μm), sealed and stood at 70° C. for 48 hr to give a medical adhesive tape.

Comparative Example 1

In the same manner as in Example 1 except that the 5% propanol/ethyl acetoacetate solution containing ethyl acetoacetate aluminum diisopropylate (crosslinking agent) or glycerol was not added, a medical adhesive tape was obtained.

Comparative Example 2

In the same manner as in Example 1 except that glycerol was not added, a medical adhesive tape was obtained.

Comparative Example 3

2-Ethylhexyl acrylate (75 parts by weight, TOAGOSEI Co., Ltd.), 2-methoxyethyl acrylate (25 parts by weight, OSAKA ORGANIC CHEMICAL INDUSTRY LTD.), ethyl acetate (100 parts by weight, Wako Pure Chemical Industries, Ltd.) and benzoyl peroxide (0.2 part by weight, NYPER BW, NOF CORPORATION) were reacted in a separable flask equipped with a condenser, a stirrer, a thermometer, a dropping funnel and a nitrogen inlet tube at 60° C. for 15 hr. under a nitrogen atmosphere to give a copolymer solution. To the copolymer solution (solid content 100 parts by weight) were added 20 parts by weight of isopropanol (Wako Pure Chemical Industries, Ltd.), which was followed by stirring.

To this solution was added 0.3 part by weight of ethyl acetoacetate aluminum diisopropylate (ALCH (Kawaken Co., Ltd.)) in a 5% isopropanol/ethyl acetoacetate (9/1(v/v)) solution.

The obtained solution was applied to a nonwoven fabric side of a support comprising a polyester nonwoven fabric (basic weight: 12 g/m$^2$) having a 2 μm thick polyethylene terephthalate film extrusion-formed thereon, to form an adhesive layer in the thickness of 80 μm and dried. The adhesive layer thus formed was adhered to a polyester film (75 μm), sealed and stood at 70° C. for 48 hr to give a medical adhesive tape.

Example 2

2-Ethylhexyl acrylate (95 parts by weight, TOAGOSEI Co., Ltd.), acrylic acid (5 parts by weight, TOAGOSEI Co., Ltd.), ethyl acetate (100 parts by weight, Wako Pure Chemical Industries, Ltd.) and benzoyl peroxide (0.2 part by weight, NYPER BW, NOF CORPORATION) were reacted in a separable flask equipped with a condenser, a stirrer, a thermometer, a dropping funnel and a nitrogen inlet tube at 60° C. for 15 hr under a nitrogen atmosphere to give a copolymer solution. To the copolymer solution (solid content 50 parts by weight) were added 0.5 part by weight of glycerol (Wako Pure Chemical Industries, Ltd.), isopropyl myristate (IPM-100, 49.35 parts by weight, Nikko chemical Co., Ltd.), and 10 parts by weight of isopropanol (Wako Pure Chemical Industries, Ltd.), which was followed by stirring.

To this solution was added 0.15 part by weight of ethyl acetoacetate aluminum diisopropylate (ALCH (Kawaken Co., Ltd.)) in a 5% isopropanol/ethyl acetoacetate (9/1(v/v)) solution.

The obtained solution was applied to a nonwoven fabric side of a support comprising a polyester nonwoven fabric (basic weight: 12 g/m$^2$) having a 2 μm thick polyethylene terephthalate film extrusion-formed thereon, to form an adhesive layer in the thickness of 80 μm and dried at 100° C. for 3 min. The adhesive layer thus formed was adhered to a polyester film (75 μm) sealed and stood at 70° C. for 48 hr to give a medical adhesive tape.

Comparative Example 4

In the same manner as in Example 2 except that the 5% propanol/ethyl acetoacetate solution containing ethyl acetoacetate aluminum diisopropylate (crosslinking agent) or glycerol was not added and the content of the isopropyl myristate was set for 50 parts by weight, a medical adhesive tape was obtained.

Comparative Example 5

In the same manner as in Example 2 except that glycerol was not added and the content of the isopropyl myristate was set for 49.85 parts by weight, a medical adhesive tape was obtained.

[2] Examples and Comparative Examples of Tape Preparation for Percutaneous Absorption Example 3

Isosorbitol dinitrate (20 parts by weight, Nihon Siber Hegner K. K.), glycerol (0.2 parts by weight, Wako Pure Chemical Industries, Ltd.), and isopropyl myristate (39.68 parts by weight, IPM-100, Nikko chemical Co., Ltd.), and isopropanol (10 parts by weight, Wako Pure Chemical Industries, Ltd.) were mixed with the copolymer solution (solid content 40 parts by weight) obtained in Example 2.

To this solution was added 0.12 part by weight of ethyl acetoacetate aluminum diisopropylate (ALCH (Kawaken Co., Ltd.)) in a 5% isopropanol/ethyl acetoacetate (9/1(v/v)) solution.

The obtained solution was applied to a nonwoven fabric side of a support comprising a polyester nonwoven fabric (basic weight: 12 g/m$^2$) having a 2 µm thick polyethylene terephthalate film extrusion-formed thereon, to form an adhesive layer in the thickness of 80 µm and dried at 100° C. for 3 min. The adhesive layer thus formed was adhered to a polyester film (75 µm), sealed and stood at 70° C. for 48 hr to give a tape preparation for percutaneous absorption.

Example 4

In the same manner as in Example 3 except that the content of glycerol was set for 0.3 part by weight and the content of the isopropyl myristate was set for 39.58 parts by weight, a tape preparation for percutaneous absorption was obtained.

Example 5

In the same manner as in Example 3 except that the content of glycerol was set for 0.5 part by weight and the content of the isopropyl myristate was set for 39.38 parts by weight, a tape preparation for percutaneous absorption was obtained.

Example 6

In the same manner as in Example 3 except that the content of glycerol was set for 1 part by weight and the content of the isopropyl myristate was set for 38.88 parts by weight, a tape preparation for percutaneous absorption was obtained.

Comparative Example 6

In the same manner as in Example 3 except that glycerol was not added and the content of the isopropyl myristate was set for 39.88 parts by weight, a tape preparation for percutaneous absorption was obtained.

Comparative Example 7

In the same manner as in Example 3 except that the content of glycerol was set for 0.1 part by weight and the content of the isopropyl myristate was set for 39.78 parts by weight, a tape preparation for percutaneous absorption was obtained.

Comparative Example 8

In the same manner as in Example 3 except that the content of glycerol was set for 5 parts by weight and the content of the isopropyl myristate was set for 34.88 parts by weight, a tape preparation for percutaneous absorption was obtained.

Example 7

Isosorbitol dinitrate (20 parts by weight, Nihon Siber Hegner K. K.), propylene glycol (0.5 part by weight, Wako Pure Chemical Industries, Ltd.), diethyl sebacate (39.38 parts by weight, Wako Pure Chemical Industries, Ltd.), and isopropanol (10 parts by weight, Wako Pure Chemical Industries, Ltd.) were mixed with the copolymer solution (solid content 40 parts by weight) obtained in Example 2.

To this solution was added 0.12 part by weight of ethyl acetoacetate aluminum diisopropylate (ALCH (Kawaken Co., Ltd.)) in a 5% isopropanol/ethyl acetoacetate (9/1(v/v)) solution.

The obtained solution was applied to a nonwoven fabric side of a support comprising a polyester nonwoven fabric (basic weight: 12 g/m$^2$) having a 2 µm thick polyethylene terephthalate film extrusion-formed thereon, to form an adhesive layer in the thickness of 80 µm and dried at 100° C. for 3 min. The adhesive layer thus formed was adhered to a polyester film (75 µm), sealed and stood at 70° C. for 48 hr to give a tape preparation for percutaneous absorption.

Comparative Example 9

In the same manner as in Example 7 except that propylene glycol was not added and the content of the diethyl sebacate was set for 39.88 parts by weight, a tape preparation for percutaneous absorption was obtained.

Example 8

2-Ethylhexyl acrylate (72 parts by weight, TOAGOSEI Co., Ltd.), N-vinyl-2-pyrrolidone (25 parts by weight, GOKYO TRADING Co., Ltd.), acrylic acid (3 parts by weight, TOAGOSEI Co., Ltd.), ethyl acetate (333 parts by weight, Wako Pure Chemical Industries, Ltd.) and azobisisobutyronitrile (0.2 part by weight, NYPER BW, NOF CORPORATION) were reacted in a separable flask equipped with a condenser, a mixer, a thermometer, a dropping funnel and a nitrogen inlet tube at 60° C. for 6 hr under a nitrogen atmosphere, and then at 76° C. for 18 hr to give a copolymer solution.

The copolymer solution (solid content 40 parts by weight) was mixed with 20 parts by weight of isosorbitol dinitrate (Nihon Siber Hegner K.K.), 0.5 part by weight of glycerol (Wako Pure Chemical Industries, Ltd.), isopropyl myristate (39.1 parts by weight, IPM-100, Nikko chemical Co., Ltd.), and 10 parts by weight of isopropanol (Wako Pure Chemical Industries, Ltd.).

To this solution was added 0.4 part by weight of titanium diisopropoxy-bis(acetylacetonate) (Tyzor AA (Du Pont)) as a 5% isopropanol/acetylacetone (9/1(v/v)) solution.

The obtained solution was applied to a nonwoven fabric side of a support comprising a polyester nonwoven fabric (basic weight: 12 g/m$^2$) having a 2 μm thick polyethylene terephthalate film extrusion-formed thereon, to form an adhesive layer in the thickness of 80 μm and dried at 100° C. for 3 min. The adhesive layer thus formed was adhered to a polyester film (75 μm), sealed and stood at 70° C. for 48 hr to give a tape preparation for percutaneous absorption.

Comparative Example 10

In the same manner as in Example 8 except that glycerol was not added and the content of the isopropyl myristate was set for 39.6 parts by weight, a tape preparation for percutaneous absorption was obtained.

Evaluation 1: Gel Fraction (1) Measurement of Gel Fraction in Ethyl Acetate

Each sample was cut into 40 cm$^2$ and the adhesive layer was weighed ($W_1$). Then the sample was immersed into ethyl acetate (100 ml) for 24 hr, and ethyl acetate was exchanged. This operation was repeated three times and the part soluble in the solvent was extracted. Then the sample was taken out, the weight ($W_2$) of the adhesive layer after drying was measured, and gel fraction was calculated by the following formula:

$$\text{gel fraction (\%)} = (W_2 \times 100)/(W_1 A/B)$$

wherein A is the total weight of the adhesive and the crosslinking agent, and B is the total weight of the adhesive, the plasticizer and the crosslinking agent.

(2) Measurement of Gel Fraction in Lactic Acid-Containing Ethyl Acetate

The gel fraction was calculated in the same manner as in the above-mentioned (1) except that a 1% lactic acid-containing ethyl acetate solution was used for immersion.

Evaluation 2: Glue Remainder after Adhesion to the Skin

Each sample of Examples 1–8 and Comparative Examples 1–10 was adhered to the chest of volunteers and peeled off after 24 hr or 48 hr. The remainder of the adhesive layer on the skin surface due to cohesive failure was visually observed. In addition, the presence of a glue remainder around the preparation was also observed.

The results of Examples 1, 2 and Comparative Examples 1–5 are shown in Table 1.

TABLE 1

| | Ex. 1 | Com. Ex. 1 | Com. Ex. 2 | Com. Ex. 3 | Ex. 2 | Com. Ex. 4 | Com. Ex. 5 |
|---|---|---|---|---|---|---|---|
| copolymer (A) | | | | | | | |
| composition | 2EHA/AA | 2EHA/AA | 2EHA/AA | 2EHA/2MEA | 2EHA/AA | 2EHA/AA | 2EHA/AA |
| composition ratio | 99.5/0.5 | 99.5/0.5 | 99.5/0.5 | 75/25 | 95/5 | 95/5 | 95/5 |
| content (parts by weight) | 99.5 | 99.5 | 99.5 | 100 | 50 | 50 | 50 |
| crosslinking agent (B) | | | | | | | |
| compound | ALCH | — | ALCH | ALCH | ALCH | — | ALCH |
| content (part by weight) | 0.3 | — | 0.3 | 0.3 | 0.15 | — | 0.15 |
| polyol compound (C) | | | | | | | |
| compound | GC | — | — | — | GC | — | — |
| content (part by weight) | 0.5 | — | — | — | 0.5 | — | — |
| plasticizer (D) | | | | | | | |
| compound | — | — | — | — | IPM | IPM | IPM |
| content (parts by weight) | — | — | — | — | 49.35 | 50 | 49.85 |
| gel fraction (%) | | | | | | | |
| in ethyl acetate | 73.5 | 0 | 72.8 | 0 | 76.3 | 0 | 75.7 |
| in lactic acid-containing ethyl acetate | 68.1 | 0 | 0 | 0 | 69.6 | 0 | 0 |
| glue remainder | | | | | | | |
| after 28 hr | none | glue remainder in entirety | none | not observed | none | not observed | observed in periphery |

TABLE 1-continued

|  | Ex. 1 | Com. Ex. 1 | Com. Ex. 2 | Com. Ex.3 | Ex. 2 | Com. Ex. 4 | Com. Ex. 5 |
|---|---|---|---|---|---|---|---|
| after 48 hr | none | not observed | observed in periphery | not observed | none | not observed | stringiness in entirety |

In Table 1, each symbol shows the following compounds.
2EHA: 2-ethylhexyl acrylate
AA: acrylic acid
2MEA: 2-methoxyethyl acrylate
ALCH: ethyl acetoacetate aluminum diisopropylate
GC: glycerol
IPM: isopropyl myristate In Examples 1, 2 and Comparative Examples 2, 5 that underwent crosslinking treatment, the gel fraction in ethyl acetate reached not less than 70%. In contrast, in Comparative Examples 1, 4 without a crosslinking agent and Comparative Example 3 wherein the adhesive did not contain carboxyl group, the gel fraction was not measurable.

The gel fraction in lactic acid-containing ethyl acetate was about 70% in Examples 1, 2 containing glycerol but gel fraction was not measurable in Comparative Examples 2, 5 without glycerol.

These samples were continuously adhered to the human skin, and as a result, a fine cohesive force was maintained in Examples 1, 2 at 24 hr and 48 hr after adhesion, with no glue remainder.

In Comparative Example 1, a glue remainder was observed at 24 hr after adhesion in the entire surface of the adhesion. Accordingly, evaluation after 48 hr was not conducted.

In Comparative Example 2, a glue remainder was not observed at 24 hr after adhesion but when the adhesion lasted for 48 hr, a glue remainder was observed in the periphery.

In Comparative Examples 3, 4, the cohesive force was clearly insufficient, and therefore, the test was not conducted.

In Comparative Example 5, stringiness was observed in the periphery at 24 hr after adhesion, and stringiness was observed in the entirety at 48 hr after adhesion.

The results of Examples 3–6 and Comparative Examples 6–8 are shown in Table 2 and the results of Examples 7, 8 and Comparative Examples 9, 10 are shown in Table 3.

TABLE 2

|  | Ex. 3 | Ex. 4 | Ex. 5 | Ex. 6 | Com. Ex. 6 | Com. Ex. 7 | Com. Ex. 8 |
|---|---|---|---|---|---|---|---|
| copolymer (A) | | | | | | | |
| composition | 2EHA/AA | 2EHA/AA | 2EHA/AA | 2EHA/AA | 2EHA/AA | 2EHA/AA | 2EHA/AA |
| composition ratio | 95/5 | 95/5 | 95/5 | 95/5 | 95/5 | 95/5 | 95/5 |
| content (parts by weight) | 40 | 40 | 40 | 40 | 40 | 40 | 40 |
| crosslinking agent (B) | | | | | | | |
| compound | ALCH | ALCH | ALCH | ALCH | ALCH | ALCH | ALCH |
| content (part by weight) | 0.12 | 0.12 | 0.12 | 0.12 | 0.12 | 0.12 | 0.12 |
| polyol compound (C) | | | | | | | |
| compound | GC | GC | GC | GC | — | GC | GC |
| content (parts by weight) | 0.2 | 0.3 | 0.5 | 1.0 | — | 0.1 | 5 |
| plasticizer (D) | | | | | | | |
| compound | IPM | IPM | IPM | IPM | IPM | IPM | IPM |
| content (parts by weight) | 39.68 | 39.58 | 39.38 | 38.88 | 39.88 | 39.78 | 34.88 |
| drug | | | | | | | |
| compound | ISDN | ISDN | ISDN | ISDN | ISDN | ISDN | ISDN |
| content (parts by weight) | 20 | 20 | 20 | 20 | 20 | 20 | 20 |
| gel fraction (%) | | | | | | | |
| in ethyl acetate | 73.5 | 74.3 | 74.6 | 69.7 | 75.0 | 73.1 | 66.1 |

TABLE 2-continued

|  | Ex. 3 | Ex. 4 | Ex. 5 | Ex. 6 | Com. Ex. 6 | Com. Ex. 7 | Com. Ex. 8 |
|---|---|---|---|---|---|---|---|
| in lactic acid-containing ethyl acetate | 61.5 | 63.2 | 63.8 | 63.9 | 0 | 55.3 | 51.6 |
| glue remainder | | | | | | | |
| after 28 hrs | none | none | none | none | observed in periphery | none | observed in periphery |
| after 48 hrs | none | none | none | none | glue remainder in entirety | stringiness | observed in periphery |

TABLE 3

|  | Ex. 7 | Com. Ex. 9 | Ex. 8 | Com. Ex. 10 |
|---|---|---|---|---|
| copolymer (A) | | | | |
| composition | 2EHA/AA | 2EHA/AA | 2EHA/VP/AA | 2EHA/VP/AA |
| composition ratio | 95/5 | 95/5 | 72/25/3 | 72/25/3 |
| content (parts by weight) | 40 | 40 | 40 | 40 |
| crosslinking agent (B) | | | | |
| compound | ALCH | ALCH | Tyzor AA | Tyzor AA |
| content (part by weight) | 0.12 | 0.12 | 0.4 | 0.4 |
| polyol compound (C) | | | | |
| compound | PG | — | GC | — |
| content (part by weight) | 0.5 | — | 0.5 | — |
| plasticizer (D) | | | | |
| compound | DES | DES | IPM | IPM |
| content (parts by weight) | 39.38 | 39.88 | 39.1 | 39.6 |
| drug | | | | |
| compound | ISDN | ISDN | ISDN | ISDN |
| content (parts by weight) | 20 | 20 | 20 | 20 |
| gel fraction (%) | | | | |
| in ethyl acetate | 73.5 | 71.1 | 69.6 | 68.9 |
| in lactic acid-containing ethyl acetate | 71.1 | 0 | 63.1 | 0 |
| glue remainder | | | | |
| after 28 hrs | none | stringiness in entirety | none | observed in periphery |
| after 48 hrs | none | stringiness in entirety | none | stringiness in entirety |

In Tables 2, 3, each symbol shows the following compound.

2EHA: 2-ethylhexyl acrylate
AA: acrylic acid
VP: N-vinyl-2-pyrrolidone
ALCH: ethyl acetoacetate aluminum diisopropylate
Tyzor AA: titanium diisopropoxy-bis(acetylacetonate)
GC: glycerol
PG: propylene glycol
IPM: isopropyl myristate
DES: diethyl sebacate
ISDN: isosorbitol dinitrate The gel fraction in ethyl acetate was not less than about 70% in the samples of Examples 3–6 and the gel fraction in lactic acid-containing ethyl acetate was not less than 60%.

The samples of Examples 3–6 were continuously adhered to the human skin, and as a result, a fine cohesive force was maintained even at 24 hr and 48 hr after adhesion, with no glue remainder.

The gel fraction in ethyl acetate was 75.0% in Comparative Example 6, but gel fraction in lactic acid-containing ethyl acetate was not measurable.

The gel fraction in ethyl acetate was 73.1% in the sample of Comparative Example 7 and the gel fraction in lactic acid-containing ethyl acetate was 55.3%.

The gel fraction in ethyl acetate was 66.1% in the sample of Comparative Example 8 and the gel fraction in lactic acid-containing ethyl acetate was 51.6%.

In Comparative Examples 6, 8, stringiness was observed in the periphery at 24 hr after adhesion, and stringiness was observed in the periphery and the entirety at 48 hr after adhesion.

In Comparative Example 7, a glue remainder was not observed at 24 hr after adhesion but when the adhesion lasted for 48 hr, a glue remainder was observed in the periphery.

From the results of the aforementioned Examples, as well as Examples 7, 8 and Comparative Examples 9, 10 using different copolymerization compositions, plasticizers and crosslinking agents, the effect afforded by the addition of a polyol compound as a crosslinking stabilizer was clear.

The medical adhesive composition of the present invention comprises a carboxyl group-containing acrylic copolymer and a small amount of a crosslinking stabilizer, is obtained by a crosslinking treatment by a metal alkoxide and a metal chelate compound, and can remarkably reduce a decrease in the cohesive force that occurs during a long-term application to the human skin. Such medical adhesive composition is preferably applied to an adhesive layer for a medical tape and a preparation for percutaneous absorption, which particularly aim at a long-term application.

This application is based on application No. 2001-259970 filed in Japan, the contents of which are incorporated hereinto by reference.

What is claimed is:

1. A tape preparation for percutaneous absorption, comprising a medical adhesive tape to be applied to human skin, which comprises an adhesive layer made from a medical adhesive composition, which medical adhesive composition comprises the following (A) to (C) as essential components:
   (A) a copolymer comprising the following (a) and (b) as copolymerized monomers,
      (a) alkyl (meth)acrylate, wherein the alkyl moiety has 4 to 18 carbon atoms, in a proportion of not less than 50 wt % of the copolymer,
      (b) a carboxyl group-containing vinyl compound in a proportion of 0.1 wt %–10 wt % of the copolymer,
   (B) an alkoxide or a chelate compound of at least a metal selected from the group consisting of titanium, zirconium, zinc and aluminum, and
   (C) a polyol compound in a proportion of 0.2 wt %–5 wt % of the medical adhesive composition,
   wherein said adhesive layer further comprises a drug to be administered by percutaneous absorption.

2. The tape preparation of claim 1, wherein the copolymer (A) further comprises
   (c) a vinyl compound free of carboxyl group, which is copolymerizable with the alkyl (meth)acrylate (a) and the carboxyl group-containing vinyl compound (b),
in a proportion of not more than 49.9 wt % of the copolymer as a copolymerized monomer.

3. The tape preparation of claim 1, further comprising a plasticizer (D) compatible with the copolymer (A), wherein a content weight ratio of the plasticizer (D) to the copolymer (A) ((D)/(A)) is 0.25–2.0.

4. The tape preparation of claim 2, further comprising a plasticizer (D) compatible with the copolymer (A), wherein a content weight ratio of the plasticizer (D) to the copolymer (A) ((D)/(A)) is 0.25–2.0.

5. The tape preparation of claim 1, wherein the polyol compound (C) is at least one of glycerol and propylene glycol.

6. The tape preparation of claim 2, wherein the polyol compound (C) is at least one of glycerol and propylene glycol.

7. The tape preparation of claim 3, wherein the polyol compound (C) is at least one of glycerol and propylene glycol.

8. The tape preparation of claim 4, wherein the polyol compound (C) is at least one of glycerol and propylene glycol.

* * * * *